(12) United States Patent
Sarangapani

(10) Patent No.: US 7,429,252 B2
(45) Date of Patent: Sep. 30, 2008

(54) OXYGEN PRODUCING DEVICE FOR WOUNDCARE

(75) Inventor: Srinivasan Sarangapani, Walpole, MA (US)

(73) Assignee: Ogenix Corporation, Cleveland, OH (US)

( * ) Notice: Subject to any disclaimer, the term of this patent is extended or adjusted under 35 U.S.C. 154(b) by 218 days.

(21) Appl. No.: 10/520,410

(22) PCT Filed: Dec. 11, 2002

(86) PCT No.: PCT/US02/39680

§ 371 (c)(1),
(2), (4) Date: Dec. 9, 2005

(87) PCT Pub. No.: WO03/049660

PCT Pub. Date: Jun. 19, 2003

(65) Prior Publication Data

US 2006/0287632 A1 Dec. 21, 2006

Related U.S. Application Data

(60) Provisional application No. 60/341,076, filed on Dec. 12, 2001.

(51) Int. Cl.
*A61F 13/00* (2006.01)

(52) U.S. Cl. ............................................. 602/2; 602/48

(58) Field of Classification Search ......... 604/304–308; 602/41–44, 48, 2
See application file for complete search history.

(56) References Cited

U.S. PATENT DOCUMENTS 5,578,022 A * 11/1996 Scherson et al. ............. 604/304
5,788,682 A      8/1998 Maget

OTHER PUBLICATIONS

International Search Report corresponding to International Application No. PCT/US02/39680.

* cited by examiner

*Primary Examiner*—Kim M Lewis
(74) *Attorney, Agent, or Firm*—Fay Sharpe LLP

(57) ABSTRACT

A device for the application of oxygen to promote wound healing and tissue repair. The device includes a portable oxygen generating device (18), which includes a cathode (10), an anode (16), and a phosphoric acid treated ion conducting membrane (14).

21 Claims, 3 Drawing Sheets

OXYGEN PRODUCING DEVICE FOR WOUNDCARE

This application is a 371 of PCT/USO2/39680, filed 12/11/02, which claims benefit of U.S. Provisional Application No. 60/341,076, filed 12/12/01.

FIELD OF THE INVENTION

The present invention relates to the promotion of wound healing on skin and tissue repair. More particularly, the present invention relates to the application of oxygen using an oxygen producing device containing a phosphoric acid treated ion conducting membrane to promote the healing of skin wounds.

BACKGROUND OF THE INVENTION

It is known that providing a supply of oxygen to a wound to or through the skin (e.g., ulcers, abrasions, cuts, sores, etc.) promotes healing of the wound. Oxygen therapy is used for inducing the growth of new skin tissue to close and heal ischemic wounds. Topical oxygen therapy calls for applying oxygen directly to an open wound. The oxygen dissolves in tissue fluids and improves the oxygen content of the intercellular fluids. Injuries and disorders which may be treated with topical oxygen include osteomylelitis, tendon and cartilage repair, sprains, fractures, burns and scalds, necrotizing fasciitis, pyoderma gangrenosum, refractory ulcers, diabetic foot ulcers and decubitus ulcers (bed sores) as well as cuts, abrasions, and surgically induced wounds or incisions.

In light of the documented benefits of such oxygen therapy, there have been several proposed methods for providing such an oxygen supply to a wound or regulating the oxygen concentration in the vicinity of a wound while also preventing contamination of the oxygen supply from the wound. Prior art teaches the application of topical hyperbaric oxygen by placing the entire affected limb of a person in a sealed chamber that features controlled pressure sealing and automatic oxygen regulation control. Not only are such oxygen chambers expensive and difficult to sterilize, however, they are also cumbersome in that the chamber must be hooked up to an external oxygen tank, limiting the patient's mobility. In addition, because the entire limb is placed in a chamber or bag, large areas of skin may be unnecessarily subjected to high levels of oxygen. Such high levels of oxygen present risks of vasoconstriction, toxicity and tissue destruction. U.S. Pat. No. 4,328,799 to LoPiano describes such a system in which a recumbent patient is connected to a gas chamber attached to an oxygen supply.

U.S. Pat. Nos. 5,578,022 and 5,788,682 describe systems in which oxygen producing devices are incorporated into a patch or bandage which is placed directly over a wound. Both these patents describe devices in which oxygen is produced electrochemically and transported across an ion conductive membrane. In such membranes, water typically provides a hydrogen bonding network and enables the rapid movement of protons through the membrane necessary for oxygen production in such a system. Water, however, has a relatively high vapor pressure and will evaporate. As water in the membrane evaporates, the membrane loses its ability to effectively conduct ions. Thus, over the course of several days, membranes used in such devices tend to lose their ability to transport oxygen. Attempting to keep the membrane hydrated can result in complications. For example, the inclusion of a water source to keep the membrane moist can make the device cumbersome, mitigating one of the key benefits of such a device. In addition, water presents a potential breeding ground for microbes. This is highly undesirable in such an oxygen generating device, which is often placed on or near open wounds that are susceptible to microbial infection.

Therefore, a need exists for a convenient and inexpensive means of maintaining the ionic conductivity of the membrane in such electrochemical oxygen producing devices over an extended period of time.

BRIEF DESCRIPTION OF THE INVENTION

In one aspect, a device for supplying oxygen for treatment of wounds to an ambulatory patient is provided, the device including a wound dressing adapted for receipt over a skin wound treatable with oxygen including a phosphoric acid treated ion conducting membrane, a portable oxygen generating device remote from said wound dressing for supplying oxygen to the skin wound, and a conduit fluidly connecting said oxygen generating device with said wound dressing.

In a second aspect, a portable, self-contained device for generating and supplying oxygen for treatment of wounds to an ambulatory patient is provided, the device including a phosphoric acid treated ion conducting membrane.

In a third aspect, a method for treating wounds using an electrochemical cell is provided, the method including the steps of bringing ambient air into contact with a porous cathode mounted in a housing, reducing oxygen present in the air to neutral species at the cathode, diffusing the neutral species through a phosphoric acid treated ion conducting membrane to a porous anode mounted in the housing, oxidizing the neutral species to oxygen at the anode, and administering a supply of oxygen to a skin wound.

The present invention relates to a process to make oxygen producing devices for wound care application. The present invention overcomes some of the inherent problems in the construction and operation of the portable, self-contained devices for the topical application of oxygen to promote wound healing described in U.S. Pat. Nos. 5,578,022 and 5,788,682. These concerns include:

An oxygen generating device for wound healing application must be thin and flexible. Thick end plates (for electrical connection and air and oxygen delivery) often used in such devices do not fulfill this requirement.

Membranes made from presently available ironically conducting polymers dry out when exposed to ambient conditions. When dry, such membranes show high ionic resistance resulting in device failure.

For wound healing application, the oxygen generating device is secured with adhesive tapes and is exposed to several impurities, which poison the catalyst for oxygen reduction and/or generation.

Many wound locations, e.g., foot, heal, lower ankle etc., call for devices that are ultra thin, so that they will not interfere with shoes and such outerwear that are part of an ambulatory patient.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof.

DETAILED DESCRIPTION OF THE PREFERRED EMBODIMENT

Figure 1:
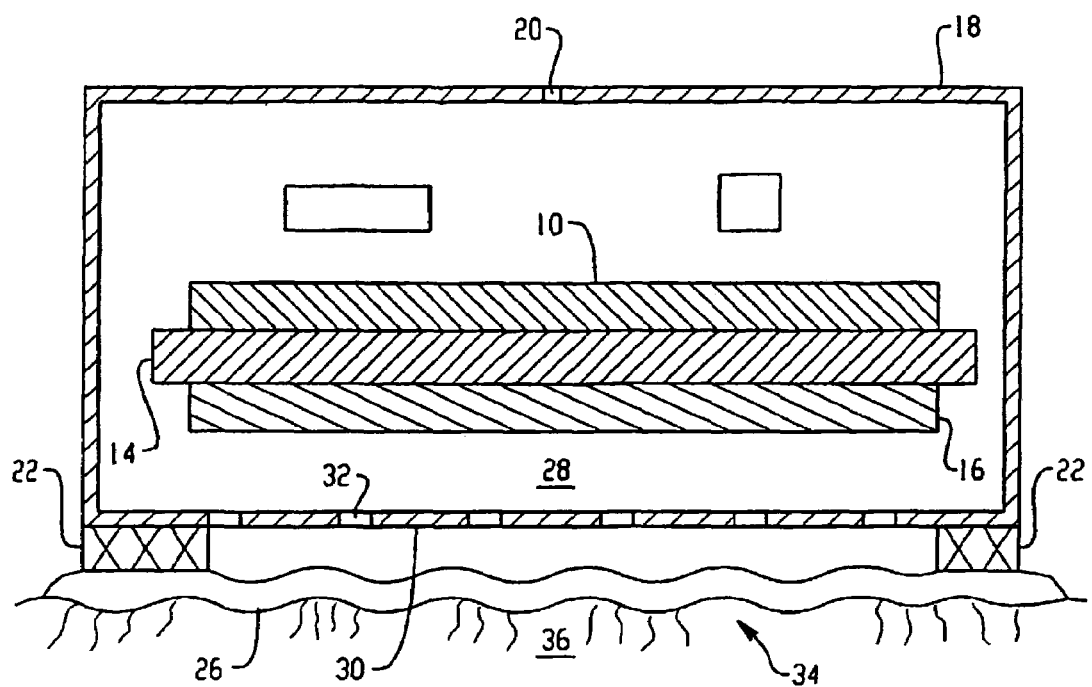
FIG. 1 is a schematic representation of a side view of an oxygen producing patch in accordance with the present invention.

Referring now to the drawings wherein the showings are for purposes of illustrating a preferred embodiment and not for purposes of limiting the same, the figures show a new approach for generating oxygen to heal wounds.

With reference to FIG. 1, a side view of an oxygen producing device and patch assembly in accordance with one aspect of the present invention is shown. The device includes a porous cathode 10, an ion conducting membrane 14 and a porous anode 16 inside a housing 18. The cathode is exposed to the atmosphere, such as through a vent 20, and the anode is exposed to or in communication with the skin wound 36. Attached to a perimeter of an underside of the housing 18 is an adhesive strip 22, which completely encircles the base and is used to secure the device to the patients skin 24 or a bandage 26 around the wound. The adhesive strip 22 does not touch the wound, but serves to cause the housing of the device to stand off a slight distance from the wound itself, such that a cavity 28 is formed between a bottom of the housing 30 and the wound. This cavity 28 becomes filled with gaseous oxygen emitted from the interior of the housing through holes 32 on the bottom of the housing 30. Alternately, instead of holes 32, the bottom of the housing 30 may be formed of a material permeable to oxygen. The adhesive strip may be permeable to oxygen gas to prevent undue gas pressure from building up in the cavity 28. This permeability may be obtained by having formed valves or capillary holes through the adhesive layer (not shown) but preferably will be obtained by having the adhesive material itself be somewhat porous, since the formed passageways may have a greater tendency to allow contaminants to enter cavity 28 when the device is not operating. The oxygen pressure in the cavity 28 will vary depending on the permeability of the housing bottom, the number of valves and the identity of the adhesive material, and the rate of oxygen production. However, the pressure will preferably not exceed about 20-30 mm Hg to prevent vasoconstriction.

Adhesive is depicted at 22 for affixing the patch over a skin wound such that oxygen cannot flow readily out of the treatment area. As stated, the patch will generally have one or more one-way valves or small capillary holes to permit outflow of air. The patch may be incorporated into, include, or be deployed on top off or underneath one or more bandage layers 34. The bandage itself may have multiple layers to promote patient comfort and healing, including but not limited to layers of cotton gauze, polyethylene oxide-water polymer, as well as layer(s) containing topical ointments and other medicinals including antibiotics, antiseptics, growth factors and living cells. Preferably, the bandage is occlusive on all sides and offers anti-microbial control without antibiotics or antiseptics, although these can still be used for added protection.

Positioned between the anode 16 and the cathode 10 is an ion conducting membrane 14. At electrode 10 a cathodic reaction occurs to combine the ambient oxygen from the air into water, in which it is present as reduced oxygen. The voltage differential created by electrodes 10 and 16 a drives the species across the membrane 14, which is specific to passage of that species. At anode 16, an anodic reaction occurs to convert the species to release the reduced oxygen as gaseous oxygen onto the wound site.

Figure 2:
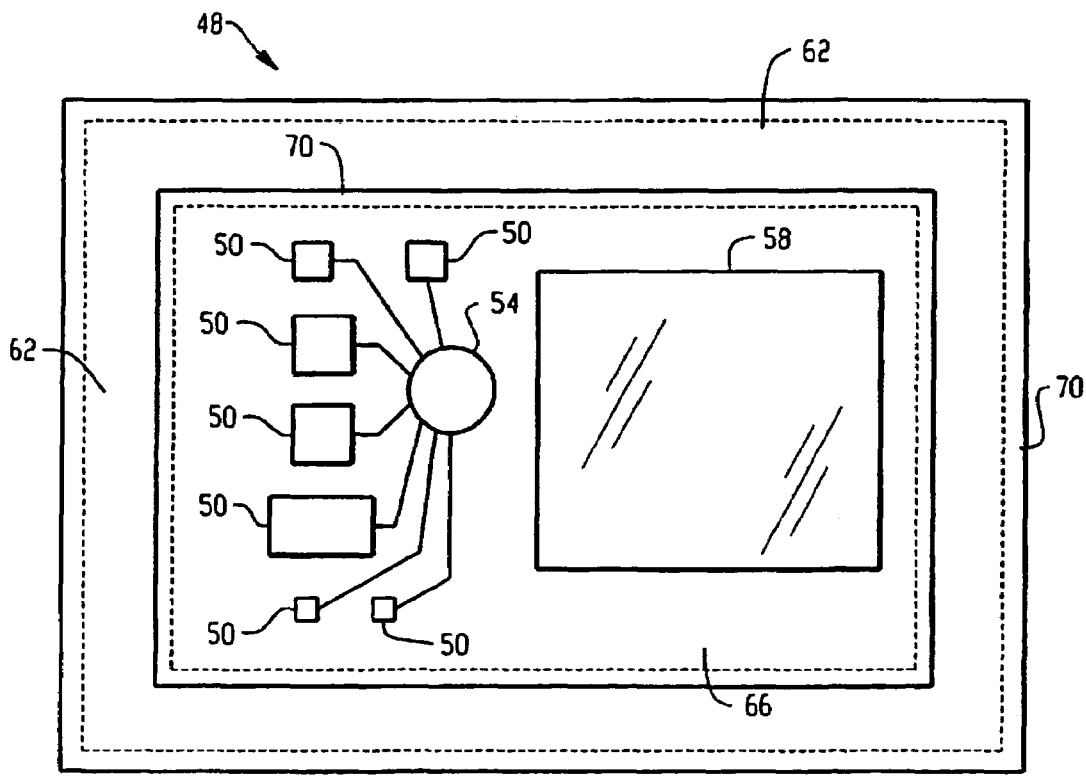
FIG. 2 is a schematic representation of a plan view of an oxygen producing patch incorporating a plurality of batteries in accordance with the present invention.

With attention now directed to FIG. 2, single patch 48 can be equipped with several sealed zinc/air batteries 50. This will enable the patient to apply oxygen intermittently as is usually the case with present treatments. Each battery may be manufactured according to a predetermined life span. For example, each of the batteries can be set to last for 1 hour, 2 hours, 4 hours, more time or less time. Differently sized batteries can be incorporated into a single patch so the same patch can be maintained in place for a period of time before the dressings are removed for cleansing of the wound. This permits differently timed dosages of oxygen to be applied to a wound. For example, a one hour therapy can take place on day 1, followed by a 2 hour therapy on day 2, and so on. Each battery includes a peel off sticker. When the sticker is removed, the zinc/air battery or other air driven battery is exposed to the air and begins operating. The oxygen generating portion, including a cathode, anode, and ion conducting membrane as described above, is depicted at 54.

In the alternative to having multiple batteries, a single battery having an electronic timing device may be included for a seven day or longer oxygen therapy treatment. Because of its monolithic construction, patches can, in principle, be manufactured in any size or shape, even including a transparent plastic window directly above the wound to visually monitor the healing progress (neovascularization) without having to remove the patch. FIG. 2 shows such a viewing or inspection window at 58. In use, the wound would be located below the window. As shown in FIG. 1, the patch can be affixed to the skin with a simple adhesive layer around the perimeter. The patch may be made in many shapes such as gloves, socks, sleeves, etc. and may be cut to size.

Figure 3:
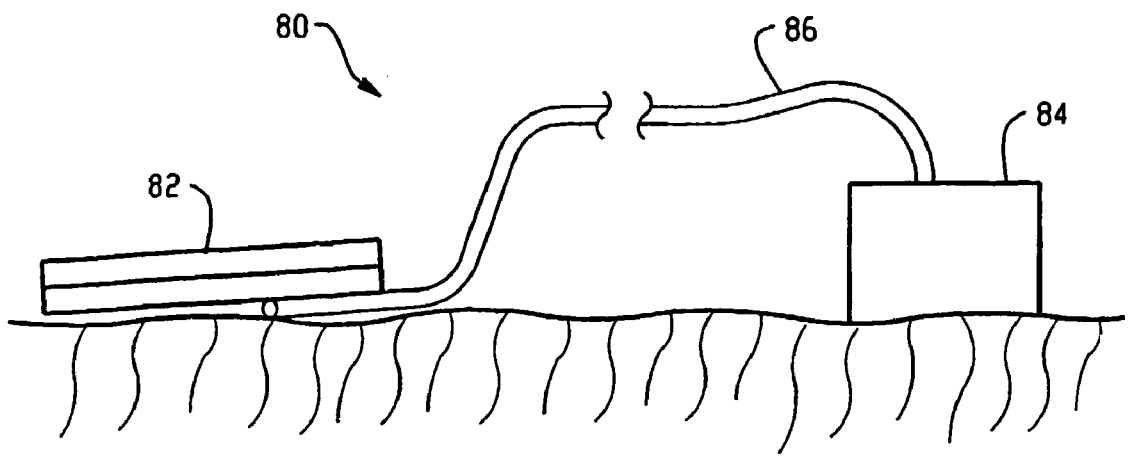
FIG. 3 is a cutaway side view of an oxygen producing patch with tubing in accordance with one embodiment of the invention deployed on a patient.

With reference to FIG. 3, an oxygen producing device and patch assembly 80 according to a second embodiment of the invention is shown generally and includes a dressing or bandage 82 to be placed over a wound, a portable oxygen producing device 84 as described above for supplying oxygen to the wound, and a conduit such as a flexible tubing 86 fluidly connecting the oxygen producing device with the bandage 82 and the underlying wound. The flexible tubing may include a Luer type connection or similar type. The tubing 86 is preferably made from a polymeric material suitable for use in hospital applications. Suitable materials for use in the tubing include, but are not limited to, silicone, polyethylene, polypropylene, polyurethane and various other thermoplastics.

Oxygen is produced at the oxygen producing device 84 via an electrochemical reaction. The oxygen then travels through the flexible tubing 86 to the bandage covered wound. Depending on the type of wound and the dressing used to cover it, the tubing can contact the dressing in various ways. For example, the end of the tubing 86 may be placed directly above the wound and under fully occlusive dressings 82, thereby making an ordinary bandage "oxygen enriched". Any type of bandage may be used, including those described above.

In other applications, the device is capable of treating venous leg ulcers where the patient must wear woven four part compression dressings to control swelling and edema. The remote oxygen producing device 84 with a tubing 86 can be placed on the top layer of the compression dressing, thus avoiding compressing the device tightly against the leg as would be necessary with prior art devices. The tubing 86 may be woven between the four individual layers of the compression dressing to conform directly to the leg without unduly compressing the oxygen generator, batteries and hardware comprising the oxygen producing device 84 against fragile skin surrounding the wound. Positioning the device on top of the compression dressing also provides the further advantage of assuring unrestricted delivery of oxygen from atmospheric air to the wound, rather than relying on atmospheric diffusion through the dressing.

The remote device can be positioned on the patient wherever convenient and comfortable. Patients with wounds on the bottom of their feet, for example, can wear a thin bandage, add the soft tubing and attach the device away from the wound on the ankle or leg. The patient is thus able to wear a shoe while being treated with oxygen without having size and comfort restraints created by the prior art. For patients with wounds to the sacrum heel, back or other pressure points, the device can be remotely placed away from the wound and pressure point for optimum comfort. Then, the relatively soft tubing can be directed to the wound site.

While microbes from a wound site may contaminate a bandage or dressing placed over it, the use of the remote device with a disposable, sterile tubing prevents microbial reflux from reaching the device. The tubing serves as a microbial barrier to the device. When in operation, the tubing provides positive gas pressure from the device to the wound and is separated by a sufficient distance to prevent reflux contamination of the device. Optionally, a microbial biofilm interrupting mechanism, such as a semi-permeable membrane may be implemented with the device within or at either end of the tubing as a further safeguard.

For in vivo uses, the end of the tubing 86 can be implanted to the site where treatment is desired. The implanted end of the tubing 86 may be perforated with multiple holes or made of material that would allow oxygen to diffuse through the tubing wall into ischemic tissue or the bloodstream. In addition, a syringe can be attached to the end of the tubing to facilitate the introduction of oxygen subdermally. Site specific oxygen delivery to promote localized angiogenesis or ischemic reperfusion and elevated metabolism is beneficial for orthopedic and organ repair as well as tissue, bone, tendon, and cartilage regeneration. Localized oxygenation of tissue and tumors for improved radiological oncology applications may benefit with the present device.

Thus, the present device may be considered a universal remote supply of oxygen in that it can be used with a wide variety of bandages or dressings already on the market. Additional types of dressings with which the present invention may be used include fully occlusive thin film dressings, hydrocolloid dressings, alginate dressings, antimicrobial dressings, biosynthetic dressings, collagen dressings, foam dressings, composite dressings, hydrogel dressings, warm up dressings, and transparent dressings. This universal property is provided by the tubing delivery pathway of oxygen, which is not known in the prior art.

Figure 4:
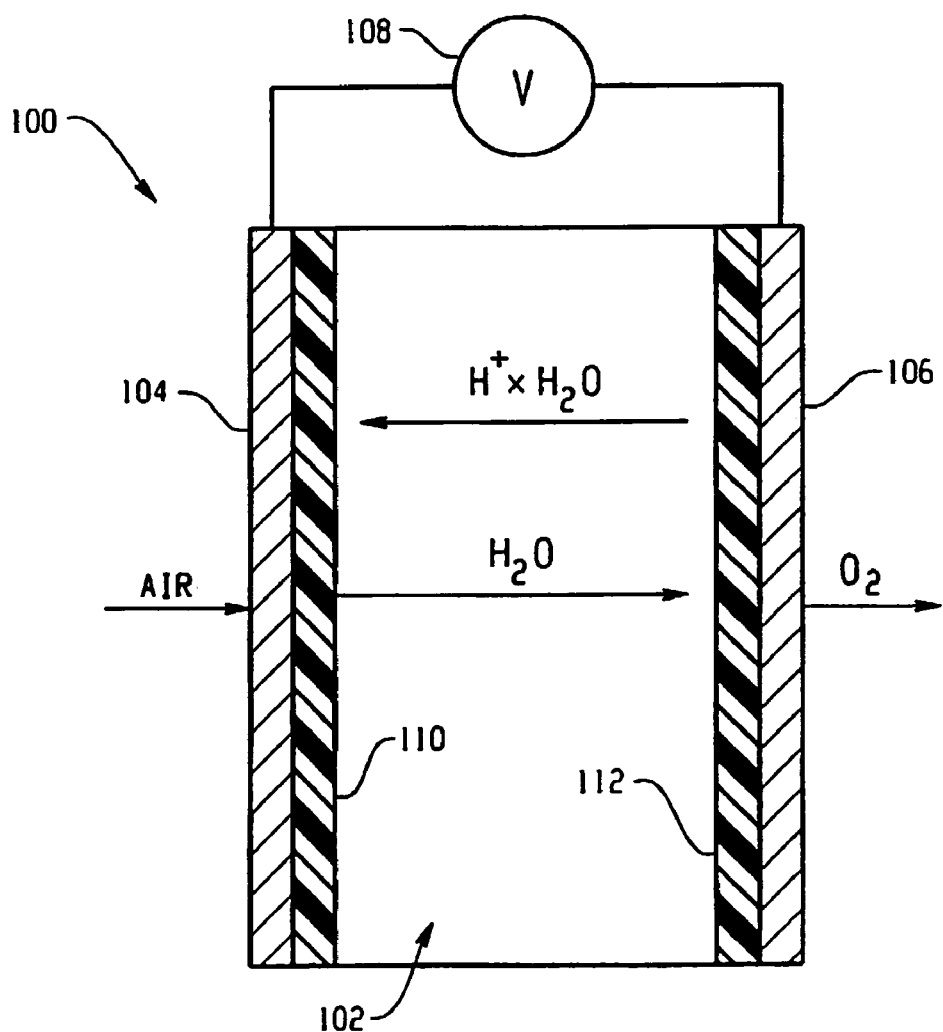
FIG. 4 is a schematic diagram of a membrane electrode assembly (MEA) for use in the oxygen generating device of shown in FIG. 2.

With reference to FIG. 4, the oxygen producing device of the present invention suitable for use in any of the above described embodiments can be described generally as comprising a membrane electrode assembly (MEA) 100 for the electrochemical production of oxygen from air or water. An ion conducting membrane 102 is positioned between two electrodes 104, 106, which in turn are connected to a power source 108, such as a battery, capable of passing a current across the electrodes.

As shown in FIG. 4, oxygen in ambient air is reduced to water at an interface region 110 between the cathode 104 held at a reducing potential and the membrane 102 using the protons supplied by the membrane according to a reaction as described below. The product water is moved through the membrane 102 to the anode 106 held at an anodic potential, which oxidizes the water back to oxygen while releasing protons at an interface region 112 between the anode and the membrane. The protons move through the membrane to the cathode 104 to make possible continued reduction of oxygen from air. Atmospheric nitrogen and carbon dioxide are electrochemically inert under the reaction conditions required for oxygen reduction and, thus, are effectively rejected at the cathode. The reduction product of oxygen alone moves through the membrane, resulting in near 100% pure oxygen on the anode. This oxygen is then directed to the tubing for delivery to a wound site.

The ion conducting membrane may be any of a number of known ion conducting membranes which are capable of conducting protons and other ionic species. Suitable membranes include various perfluoronated ionomer membranes that include a poly(tetrafluoroethylene) backbone and regularly spaced perfluoronated polyether side chains terminating in strongly hydrophilic acid groups. A preferred group of membranes suitable for use in the present invention include those containing sulfonic acid terminating groups on the side chains and available under the trademark Nafion® from E.I. Dupont Co. Nafion® is a perfluorinated polymer that contains small proportions of sulfonic or carboxylic ionic functional groups. Its general chemical structure can be seen below, where X is either a sulfonic or carboxylic functional group and M is either a metal cation in the neutralized form or an $H^+$ in the acid form. Other suitable membranes include partially fluorinated membrane materials and those based on hydrocarbon polymer backbones.

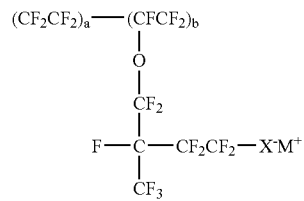

The following reaction mechanisms may be used in the present invention for the production of oxygen including:

At the cathode: $O_2 + 4H^+ + 4e^- \rightarrow 2H_2O$

At the anode: $2H_2O \rightarrow O_2 + 4H^+ + 4e^-$ with the net reaction being the depletion of a gaseous oxygen (from ambient air) on one side of the membrane and an increase of the oxygen concentration on the other side.

The electrodes used in the membrane electrode assembly can be in the form of a mesh or a thin coating on the opposite surfaces of the membrane. They can be made of any materials which are electrically conductive and which will catalyze the reduction of gaseous oxygen into water, provide a voltage differential across the membrane to move the oxygen containing species and catalyze the oxidation of the product water to release oxygen. Suitable electrode materials include, but are not limited to, platinum, iridium, rhodium ruthenium as well as their alloys and oxides in a pure finely divided form or as supported catalysts.

Figure 5:
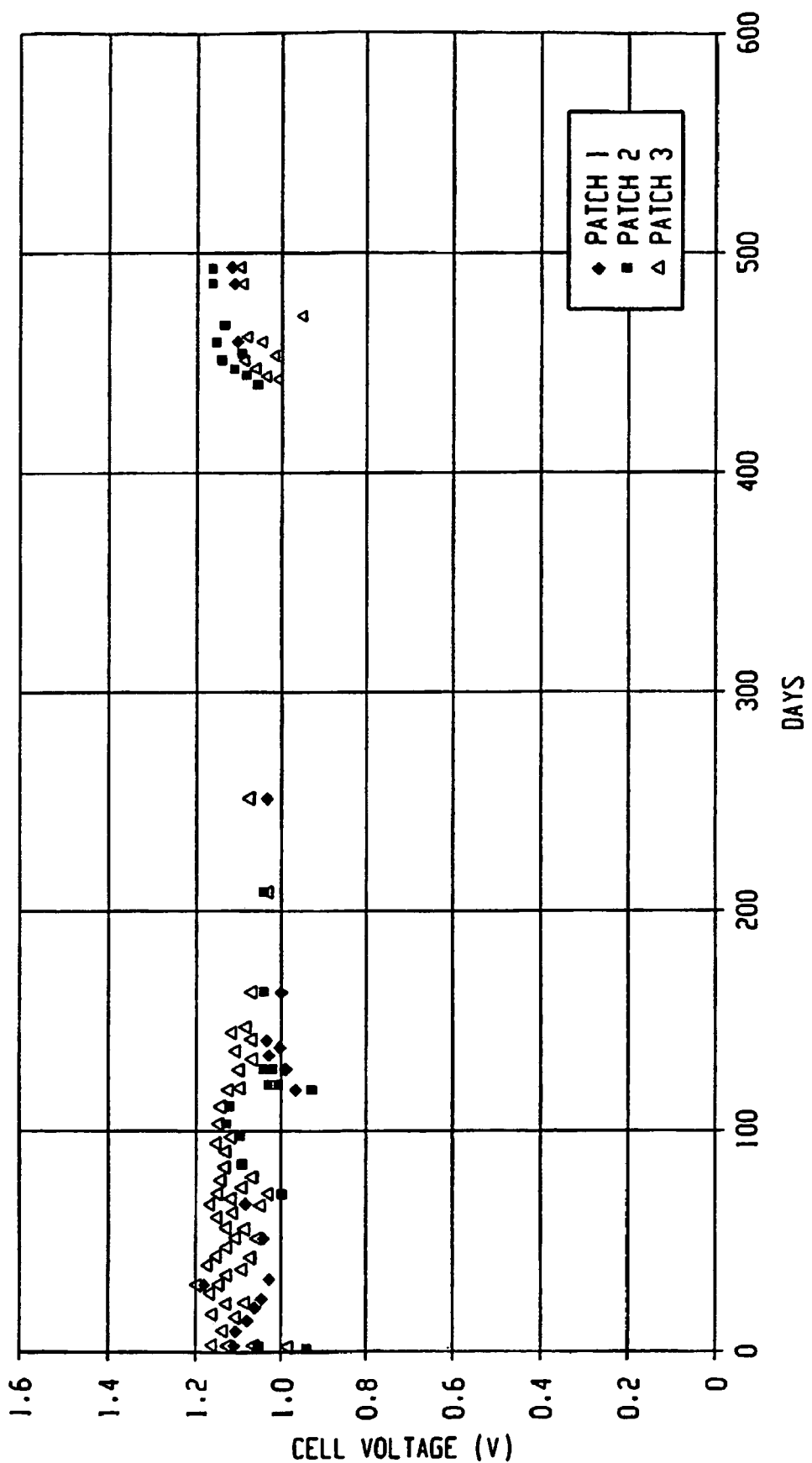
FIG. 5 is a graph showing life test data with patch assemblies according to the present invention.

In one embodiment of the present invention, Nafion® membrane is treated or imbibed with 85-100% Phosphoric acid. In Nafion®, water normally provides the hydrogen bonding network and enables the rapid movement of protons through the polymer (and hence the high ionic conductivity). However, when left under ambient conditions, Nafion® loses water to the surroundings (due to the relatively high vapor pressure of water), which results in the loss of ionic conductivity. Phosphoric acid can also provide a hydrogen bonding network similar to that of water, but unlike water, has a very low vapor pressure—at room temperature the vapor pressure of phosphoric acid is so low that it can be considered zero. It is also hygroscopic to a degree, such that it may absorb water from the atmosphere. This combination of properties makes it possible to replace most of the water in Nafion® with phosphoric acid under appropriate conditions. Nafion®, thus treated with phosphoric acid continues to provide adequate ionic conductivity when exposed to ambient conditions for extended periods of time (several months). The effect of this can be seen in FIG. 5, which shows that such oxygen producing devices utilized with bandages in the treatment of wounds maintained a steady voltage (and hence continued to generate oxygen) for up to 500 days at a constant applied current of 15 mA. The intrinsic conductivity of a phosphoric acid imbibed Nafion® is much lower than that of water imbibed Nafion® at room temperature. For low current density applications such as the present usage, however, this decreased conductance is quite acceptable.

The electrochemical process is driven by the battery 50. The battery may comprise a plurality of sealed zinc/air batteries. This enables the patient to apply oxygen intermittently, as is usually the case with present treatments. Each battery may be manufactured according to a predetermined life span. For example, each of the batteries can be set to last for 1 hour, 2 hours, 4 hours, or other time periods. Different sized batteries may be incorporated into a single oxygen producing device. This permits differently timed dosages of oxygen to be applied to a wound. Each battery may include a peel off sticker that, when removed, exposes the battery to air and begins operating. Reversing the polarity of the battery will reverse the process so that a very low level of oxygen (as low as about 0% oxygen concentration) is supplied to the wound, thereby modulating the level of oxygen in the wound treatment area. The modulation of the level of oxygen will control the rate of wound healing by increasing or decreasing the oxygen tension in the tissues that stimulate healing. Other types of power sources include batteries, fuel cells, photovoltaic cells and supercapacitors in combination with one or more of the above power sources.

The conventional method of making a membrane electrode assembly that is capable of accomplishing the above goal consists of bonding a Pt/C electrode and a Pt black electrode to either side of a Nafion® 117 (or similar) membrane. The electrical connections from the electrodes to the voltage source are normally provided through conducting end plates that are normally made of thick graphite or metallic material. To reduce weight and improve mobility of the device, a thin (e.g., 1-5 mil), electronically conducting and electrochemically inert wire is placed in between the membrane and electrode during the bonding process, thereby making the electrical connection an integral part of the membrane electrode assembly. Examples of such wires include: gold, Pt, gold or Pt plated or deposited Ta, and similar materials.

In addition, a catalyst is used to improve the electrochemical production of oxygen in the above reactions. The addition of a catalyst in one or both electrodes aids in overcoming the kinetic reaction barriers. Preferably, a Pt—Ru, Pt—Ir, or similar noble metal alloy catalysts that is poison resistant is used to coat the electrodes. The use of such poison resistant catalysts will prevent impurities introduced from the adhesive and other components of the device from reducing the catalyst activity and deactivating the device. Suitable non-limiting examples of anode catalysts include Pt—Ir, Pt—Sn, and ternary combinations thereof. Suitable non-limiting examples of cathode catalysts include Pt—Ru/C, Pt—Sn, Pt—Ir, Pt—C, and ternary combinations thereof. A preferred catalyst is Pt—Ir.

An electronic PC board or controller (not shown) may be incorporated into the device and can contain an on-off switch and a current monitoring port. The amount of oxygen generated by the device can be varied by changing the voltage applied across the electrodes. Typically, the device will produce between about 1 and about 50 ml oxygen/hr, more preferably between about 1 and about 10 ml/hr.

The device and design as taught in this application has clear advantage over a conventional means of delivering oxygen, i.e., a tank filled with oxygen placed in proximity to the wound. For example, for a treatment regime of 3 weeks, the amount of oxygen required could range anywhere between 2100 cc to 6,300 cc. Typical weight efficiency of high pressure storage containers are 2%. To store 2.1 liters of oxygen, the total weight of the container alone will be ~300 grams. The weight of the regulator system for such high pressure will add additional weight. To store 2 liters of oxygen in a 50 ml volume, we have to pressurize the container to 40 atmospheres. It is clear therefore, from weight, volume and safety standpoints, high pressure oxygen storage is not the best way to practice oxygen delivery bandages for ambulatory patients.

In addition to the reduced weight, the oxygen producing device of the present invention allows precise control of the amount of oxygen that reaches a wound. By setting a low flow rate, the wound is discouraged from drying out, allowing for a moist wound healing process, which is the standard preferred method. This controlled, slow oxygen gas flow from the device can not be easily replicated using compressed oxygen cylinders. The lowest flow rates from commercially available pressure regulators fitted to compressed gas cylinders flow far too much gas to be used in moist wound healing applications or in vivo uses. The bulk weight and attendant fire hazard associated with compressed cylinders also make such a system unsuitable for wound healing or internal medicine.

The methods used for generating and depleting oxygen are preferably electrochemical in nature, although nonelectrochemical methods may be used to administer the oxygen to treatment area. For example, chemically or thermally induced reactions that could release or absorb oxygen in a controlled fashion may be employed.

The invention has been described with reference to various preferred embodiments. Obviously, modifications and alteration will occur to others upon a reading and understanding of this specification. It is intended to include all such modifications and alterations insofar as they come within the scope of the appended claims or the equivalent thereof.

What is claimed is:

1. A device for supplying oxygen to a patient for treatment of a wound or condition comprising:
   a wound dressing adapted for receipt over a wound or injury treatable with oxygen;
   a portable oxygen generating device remote from said wound dressing for supplying oxygen to the skin wound, said device comprising an anode, a cathode, a power source and a phosphoric acid treated ion conducting membrane for electrochemically producing oxygen;
   a conduit fluidly connecting said oxygen generating device with said wound dressing.

2. A device for supplying oxygen according to claim 1, wherein said conduit is a flexible tubing.

3. A device for supplying oxygen according to claim 2, wherein said wound dressing is a woven four part compression dressing for treating venous ulcers.

4. A device for supplying oxygen according to claim 2, wherein said tubing is woven between the individual layers of the compression dressing.

5. A device for supplying oxygen according to claim 2, wherein said oxygen is delivered subdermally.

6. A device for supplying oxygen according to claim 2, further comprising a syringe fluidly connected to an end of said tubing for subdermal delivery of oxygen.

7. A device for supplying oxygen according to claim 2, further including a semipermeable membrane for preventing microbial reflux into the oxygen producing device.

8. A device for supplying oxygen according to claim 2, wherein the production of oxygen occurs according to a four electron process.

9. A device for supplying oxygen according to claim 2, wherein said ion conducting membrane is a perfluorinated ionomeric membrane.

10. A device for supplying oxygen according to claim 2, wherein said power source applies a current across said cathode and anode.

11. A device for supplying oxygen according to claim 2, further including a catalyst in at least one of said anode and cathode.

12. A device for supplying oxygen according to claim 11, wherein said catalyst comprises Pt-Ir.

13. A device for supplying oxygen according to claim 2, wherein said device generates between about 1 to about 50 ml oxygen/hr under standard temperature and pressure.

14. A device for supplying oxygen according to claim 2, wherein said device is capable of producing oxygen for several weeks without the addition of water to the device.

15. A device for supplying oxygen according to claim 2, wherein said tubing is perforated with a plurality of holes for in vivo treatment.

16. A device for supplying oxygen according to claim 2, wherein said oxygen generating device is mounted on a patient.

17. A device according to claim 1, wherein a catalyst is associated with said anode and is selected from the group consisting of Pt-Ir, Pt-Sn, and ternary combinations thereof.

18. A device according to claim 1, wherein a catalyst is associated with said cathode and is selected from the group consisting of Pt-Ir, Pt-Sn Pt-Ru/C, Pt-C, and ternary combinations thereof.

19. A device for supplying oxygen to a patient for treatment of a wound or condition comprising:
    a wound dressing adapted for receipt over a wound or injury treatable with oxygen; and
    a portable oxygen generating device for supplying oxygen to the wound, said device comprising an anode, a cathode, a power source and a phosphoric acid treated ion conducting membrane for electrochemically producing oxygen.

20. A device for supplying oxygen according to claim 19, wherein said device generates between about 1 to about 10 ml oxygen/hr under standard temperature and pressure.

21. A method for treating wounds or conditions using an electrochemical cell, comprising the steps of:
    bringing ambient air into contact with a porous cathode mounted in a housing;
    reducing oxygen present in the air to neutral species at the cathode;
    diffusing the neutral species through a ion conducting membrane to a phosphoric acid treated porous anode mounted in the housing;
    oxidizing the neutral species to oxygen at the anode; and
    administering a supply of oxygen from the anode to a dressing and an underlying wound or injury.

* * * * *